United States Patent [19]

Khanna et al.

[11] 4,318,846

[45] Mar. 9, 1982

[54] NOVEL ETHER SUBSTITUTED FLUORESCEIN POLYAMINO ACID COMPOUNDS AS FLUORESCERS AND QUENCHERS

[75] Inventors: Pyare Khanna, Mountain View; Edwin F. Ullman, Atherton, both of Calif.

[73] Assignee: Syva Company, Palo Alto, Calif.

[21] Appl. No.: 73,163

[22] Filed: Sep. 7, 1979

[51] Int. Cl.³ .................. A61K 39/385; A61K 39/44; C07G 7/00
[52] U.S. Cl. ............................ 260/112 B; 23/230 B; 260/112 R; 260/112.5 R; 260/112.7; 260/121; 424/8; 424/12; 424/85; 424/88; 435/7; 435/188; 525/420; 260/335
[58] Field of Search ............... 260/112 R, 112 B, 121; 424/85, 88; 525/420; 435/188

[56] References Cited

U.S. PATENT DOCUMENTS 4,174,384 12/1979 Ullman et al. .................. 260/112 B
4,220,450 9/1980 Maggio .............................. 435/7 X
4,220,722 9/1980 Rowley et al. ..................... 435/7 X

*Primary Examiner*—Howard E. Schain
*Attorney, Agent, or Firm*—Bertram I. Rowland

[57] ABSTRACT

Diether symmetrically substituted fluoresceins are provided having at least one anionic group and a linking functionality. Depending upon the site of substitution, the compounds can be used as fluorescers absorbing at wavelengths in excess of 500 nm or as quenchers, absorbing at wavelengths in excess of 500 nm and exhibiting substantially no fluorescence. The compounds find wide application, particularly as labels in fluorescent immunoassays.

22 Claims, No Drawings

NOVEL ETHER SUBSTITUTED FLUORESCEIN POLYAMINO ACID COMPOUNDS AS FLUORESCERS AND QUENCHERS

BACKGROUND OF THE INVENTION

1. Field of the Invention

Fluorescing compounds find wide application, because of their ability to emit light upon excitation with energy within certain energy ranges. By virtue of this ability, fluorescers have found employment in advertising, novelty items, and as labels in chemical or biological processes, e.g. assays. That is, various compounds can be conjugated to a fluorescing compound, the conjugate subjected to some type of partitioning, and the fate of the conjugate determined by irradiating the sample with light and detecting the zone in which the conjugate exists.

This technique can be employed in immunoassays, involving specific binding pairs, such as antigens and antibodies. By conjugating a fluorescer to one of the members of the specific binding pair and employing various protocols, one can provide for partitioning of the fluorescer conjugate between a solid phase and a liquid phase in relation to the amount of antigen in an unknown sample. By measuring the fluorescence of either of the phases, one can then relate the level of fluorescence observed to a concentration of the antigen in the sample.

Alternatively, one can avoid partitioning of the fluorescent label by providing for a mechanism which varies the fluorescence of the label, depending upon the label environment in a liquid medium. For example, in addition to labeling one of the members of the specific binding pair with the fluorescer, one may label the other member with a quencher, that is, a molecule which is able to absorb the excitation energy of the fluorescer molecule, preventing the emission of a photon. The quenching then will occur only when the two members of the specific binding pair are associated, so that fluorescer and quencher have the required spatial proximity for quenching.

In preparing fluorescers, there are many desiderata. For a fluorescer, one desires a high extinction co-efficient, a high quantum efficiency, preferably approaching or equal to one, chemical stability, a large Stokes shift, and, where the fluorescence is to be affected by another agent, an efficient response to such reagent. Furthermore, where the fluorescer is to be used in the presence of serum or other composition, which is in itself fluorescent, it is desirable that the fluorescer absorb energy in a substantially different range from that absorbed by the other compounds in the medium. In the case of serum, it is desirable to have fluorescers which absorb light substantially in excess of 450 nm, preferably in excess of 500 nm.

For quencher molecules, it is desirable that the quencher efficiently quench the fluorescer molecule, that is, that there be substantial overlap between the wavelength range of emission of the fluorescer and the wavelength range of absorption by the quencher. In addition, the quencher should be chemically stable, preferably non-fluorescent, and provide a fluorescer-quencher pair with a high quenching efficiency.

In addition, any compounds of interest should be susceptible to reasonable modes of synthesis to provide the desired product in substantially pure form.

2. Description of the Prior Art

U.S. Pat. No. 3,998,943 discloses an immunoassay involving a ligand-fluorescer conjugate employing steric inhibition of simultaneous binding of antibody for ligand and antibody for fluorescer, where the antibody for fluorescer substantially quenches the fluorescence. U.S. Pat. No. 3,996,345 describes an immunoassay involving fluorescer-quencher pairs, where a fluorescer is bonded to one member of a specific binding pair and a quencher bonded to the same or different member of a specific binding pair. The assay is dependent upon the degree to which the quencher and fluorescer are brought within quenching proximity based on the amount of analyte in the medium.

There is an extensive list of compounds involving derivatives of fluorescers. Known compounds include 4',5'-dihydroxyfluorescein and 4',5'-dihydroxy-2',7'-dibromofluorescein (C.A. 61, 7407d). Isothiocyanate derivatives of fluorescein are commercially available, while isocyanate derivates are described in C.A. 59, 563b and sulfonic derivatives are described in C.A. 58, 9012a.

SUMMARY OF THE INVENTION

Di(chalcogen ether) symetrically substituted fluoresceins are provided having at least one anionic group and one functionality for linking to another molecule. The compounds are linked to other materials for reagents in immunoassays, particularly immunoassays involving serum samples. The fluorescein compounds may also be halogenated.

The fluorescers have large extinction coefficients, high quantum yields, have absorption maxima above 500 nm, have Stokes shifts, normally in excess of 10 nm and are stable by themselves and when bonded to other compounds. The quenchers have absorption maxima above 500 nm, have little or no observable fluorescence and efficiently quench a broad spectrum of fluorescent compounds.

DESCRIPTION OF SPECIFIC EMBODIMENTS

The subject invention concerns chromogenic di(chalcogen ether) symmetrically substituted fluorescein compounds capable of accepting or donating electronic energy, which find particular use when conjugated to other compounds, particularly polypeptides, or soluble or insoluble supports for use as reagents in immunoassays. The fluorescein compounds are unsubstituted at 1',8' and are symmetrically disubstituted on the xanthene ring at either the 4',5'- or the 2',7'-positions. The compounds are normally 2,7-di(aliphatic ether substituted) or 4,5-di(aliphatic ether substituted)-9-phenyl-6-hydroxy-3H-xanthene-3-ones.

The molecules will have at least 15 carbon atoms, usually at least 16 carbon atoms, and not more than about 45 carbon atoms, usually not more than about 35 carbon atoms. There will be at least 5 chalcogen atoms (atomic number of 8 to 16, oxygen and sulfur), of which at least 3 will be oxygen. In addition to the chalcogen atoms, there may be from 0 to 8, usually from 0 to 6 heteroatoms, such as nitrogen, halogen of atomic number 9 to 53, particularly of 17 to 53, that is, fluorine, chlorine, bromine and iodine, or other heterofunctionalities which may be present to provide specific effects. There will usually be at least one anionic group, normally carboxylate or sulfonate, and one linking group, inter alia non-oxo-carbonyl, including isothiocyanate and isocyanate; sulfonamide, mercapto, and amino, which may or may not be bonded directly to an annular carbon atom. For the most part, the linking group will be on the group, usually phenyl, substituted at the nine position of the xanthene, although linking groups may also be present as substituents on the ether group. These compounds are conjugated to haptens and antigens to provide conjugates which are capable of fluorescing or of quenching a fluorescer when the quencher is in close spatial proximity to the fluorescer.

The subject compositions have absorption maxima above 500 nm, usually above 510 nm, with relatively narrow bands, usually at least 50% of the area of the longest wave length absorption being over a wavelength range of about 50 nm. The fluorescing compounds are characterized by having good chemical stability, large Stokes shifts and extinction coefficients in excess of 65,000, usually in excess of 75,000. The Stokes shifts will be at least 10 nm, and preferably at least about 20 nm. The quenching compounds, will fluoresce with a quantum efficiency less than 10%, preferably less than 5%, in 0.05 molar phosphate when irradiated with light at the absorption maximum.

The compounds of the subject invention provide novel compounds having important spectroscopic and physical properties. The compounds have absorption maxima above 500 nm. By choosing the positions for the oxy substituents one can provide highly fluorescent compounds or compounds that are substantially non-fluorescent and can be used as quenchers. Compounds with ether substituents at the 2',7'-positions (fluorescein numbering) provide fluorescent compounds with high quantum efficiencies. Compounds with ether substituents at the 4',5'-positions provide compounds with substantially no fluorescence, while absorbing at long wavelengths so as to act as efficient quenchers.

For the most part the compounds of this invention will be water or base soluble compounds having the following formula:

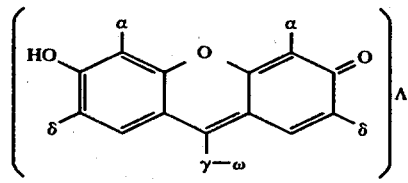

wherein:
each of the α's and each of the δ's may be the same or different, either the α's or the δ's being bonded to an annular carbon atom through a chalcogen (atomic number 8 to 16, oxygen and sulfur); when not the chalcogen bonded pair the α's may be any substituent other than chalcogen and the δ's may be any convenient functionality including chalcogen; one of the α's or δ's bonded through an ether or ω may be taken together with Λ to provide an active functionality for linking or, when not taken together with Λ, may be a linking functionality to Λ; when not taken together with Λ, ω may be any non-interfering functionality or hydrogen;

Λ is a ligand or receptor when not taken together to form an active functionality for linking;

γ is a bond, or a spacer arm of from about 1 to 20 atoms, usually 1 to 16 carbon atoms; usually an aliphatic (includes cycloaliphatic) group of from 1 to 7 carbon atoms having more than 4 annular carbon atoms when cycloaliphatic or an aromatic group of from 6 to 16, usually 6 to 10 annular atoms;

there being one or more of the group in the parenthesis bonded to Λ when Λ is a ligand or receptor.

With the quencher molecules, the 4,5-diether-6-hydroxy-3H-xanthen-3-ones, the presence or absence of a substituent at the 2 and 7 positions does not affect the quenching, but can be used to modify the absorption characteristics of the molecule. Therefore, when the αs are ethers, the δs may be hydrogen or any convenient substituent such as alkyl of 1 to 6 carbon atoms, oxy (hydroxy and alkoxy of 1 to 6 carbon atoms), thio (mercapto, alkylthio of 1 to 6 and sulfonic acid, ester and amide), non-oxo-carbonyl of 1 to 6 carbon atoms (includes acid, esters and amides), cyano, nitro, halo, oxo-carbonyl of 1 to 6 carbon atoms, or combinations thereof. The choice of substitution will be governed by the resulting absorption maximum, synthetic convenience and the effect on the physical and chemical properties of the molecule, such as water solubility, chemical reactivity, oxidation sensitivity and the like.

With the fluorescer molecule, the substituents at the 4,5-positions may be varied widely so long as the fluorescent efficiency is not significantly adversely affected. Therefore, while the substituents may be widely varied, the 4,5-position should not be substituted with chalcogen, which would have the effect of substantially reducing the fluorescence of the molecule. Therefore, the range of substituents for the 4,5-position of the fluorescer is more restricted than the range of substituents for the 2,7-position of the quencher.

For the most part, the compounds of this invention having γ as aromatic will have the following formula:

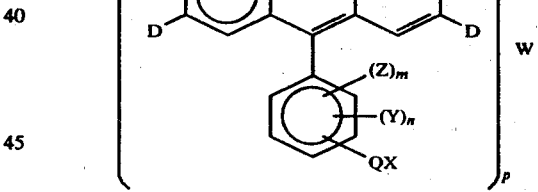

wherein:
the two As are the same or different, normally being the same, when other than the functionality for linking;

the two Ds are the same or different, normally being the same, when other than the functionality for linking;

either the As or the Ds are chalcogen ethers (chalcogen of atomic number 8 to 16), usually oxyethers, of the formula —JMX, where J is oxygen or sulfur;

when other than —JMX, the As are hydrogen or halo of atomic number 9 to 53 i.e. fluorine, chlorine, bromine, or iodine, particularly chloro and iodo, while the Ds may be hydrogen or any substituent, particularly having carbon and hydrogen and as heteroatoms, oxygen, sulfur, nitrogen and halogen, normally chemically inert under conditions of usage;

M is a divalent hydrocarbon group, normally saturated aliphatic, of from 1 to 8, usually 1 to 6 and preferably 1 to 3 carbon atoms, usually straight chain;

one of the X's is an active functionality for linking to a ligand, receptor, or support or a functionality linked to said ligand or support;

wherein when X is taken together with W to provide an active functionality for linking, XW can be a non-oxo-carbonyl functionality including the sulfur and nitrogen analogs thereof, e.g. carboxylic acid, carboxylic acid ester, e.g. lower alkyl (1–3 carbon atoms) or active ester capable of forming amide bonds in an aqueous medium, e.g. N-oxy succinimide and p-nitrophenyl, isocyanate, isothiocyanate, imidate lower alkyl ester; activated olefin, e.g. maleimido; mercaptan (—SH); formyl (—CHO); sulfonyl chloride; amino; active halo e.g. haloacetyl or halotriazine, with the proviso that XW is non-oxo-carbonyl or sulfonyl when bonded to M;

when X is not taken together with W, one of the Xs is a linking functionality bonded to W and depending upon the particular active functionality will be non-oxo-carbonyl (including the nitrogen and sulfur analogs thereof) having one valence to carbon; carbamyl, thiocarbamyl; substituted ethylene from activated olefin; thio; methylene (from formyl by reductive amination); amido nitrogen or sec-amino; sulfonyl; or oxo-carbonyl methyl from active halo; when X is a linking functionality bonded to M, X is non-oxo-carbonyl; when not a linking group, X is hydrogen or non-oxo-carbonyl, e.g. carboxylic acid, ester or amide, sulfonamide, sulfonic acid or, particularly when bonded to an annular carbon atom, halo;

$p$ is one when W is taken together with X and is otherwise on the average 1 to the molecular weight of W divided by 500, usually 1000, more usually 1500 and most usually 2000, generally $p$ ranges from about 1 to 200, usually 1 to 100;

when W is not taken together with X, W is a ligand, including receptors, of at least about 125 molecular weight, being haptenic or antigenic, generally being from about 125 to 2000 molecular weight when haptenic and from about 5000 to $1 \times 10^7$ when antigenic, although combinations of antigens and other materials may have a much higher composite molecular weight; the ligand will be joined to X, normally through amino, hydroxy, mercapto or active ethylene, to form amido, amidine, thioamide, ether, or thioether, although other linkages may be employed, or W is a soluble or insoluble support which may be a polysaccharide, naturally occurring or synthetic, modified or unmodified, a naturally occurring or synthetic polymer, glass, inorganic solids, liposomes, or the like;

Q is a bond or spacer arm (linking chain), usually aliphatic, aromatic, heterocyclic, or combination thereof, generally aliphatically saturated, where the arm will usually have from 1 to 16, more usually 1 to 12, preferably 1 to 8 atoms in the chain, which are carbon, nitrogen, oxygen and sulfur, wherein the nitrogen is amido or bonded solely to carbon and hydrogen, e.g. tert-amino, oxygen is oxy, and sulfur is thioether, with the chalcogen bonded solely to carbon and heteroatoms being separated by at least two carbon atoms when bonded to saturated carbon atoms; the total number of carbon atoms being generally 1 to 20 usually 1 to 12 and the total number of heteroatoms being 0 to 10, usually 0 to 8; oxygen may be present as non-oxo-carbonyl or oxy, there being from 0 to 9, usually 0 to 4 heterofunctionalities; when X is not a linking functionality or group, Q will normally be a bond;

Y is halogen of atomic number 9 to 53, particularly chloro;

$n$ is an integer of from 0 to 4 wherein m plus n is not greater than 4;

Z is an acidic anionic group, such as carboxylic acid or sulfonic acid; and $m$ is an integer of from 0 to 3, usually 1 to 3.

Quite obviously, the compounds of the subject invention can be modified so as not to be within the above formula, without significantly affecting the properties of the compounds. For example, one or more of the acidic anionic groups could be esterified or amidified, or alkyl groups can be substituted on the phenyl, as well as other groups, such as cyano, nitro, or the like. However, these changes will in most cases require additional synthetic steps which are not warranted by the degree of enhancement, if any, in the spectroscopic or chemical properties of the resulting product.

The subject compounds have many desirable properties. The products have significant water solubility which allow them to be conjugated to a wide variety of polypeptides, without significantly adversely affecting the water solubility of the polypeptide, nor having the polypeptide adversly affect the spectroscopic properties of the subject compounds.

As for the spectroscopic properties of the compounds, the compounds absorb at relatively long wavelengths, generally in excess of 500 nm, more usually in excess of 510 nm. Thus, naturally occurring fluorescence which may be encountered when working with physiological fluids is substantially avoided by employing exciting light at a wavelength range which does not significantly excite the naturally occurring fluorescers. In addition, the compounds have relatively sharp absorption peaks, and the fluorescers relatively sharp emission peaks. Because of this, efficient overlap can be obtained between fluorescers and quenchers which allow for efficient quenching up to distances of about 70 Å. The fluorescing compounds also have large Stokes shifts, so that the absorption band and emission band peaks are separated by at least 10 nm, frequently by at least 15 nm. The large Stokes shifts minimize background interference with the observed fluorescence.

The quenchers have little or no fluorescence, so they do not contribute to background interference with the observed signal. By providing for fluorescer-quencher couples, where the absorption band of the quencher substantially overlaps the emission bands of the fluorescer, efficient systems are provided for performing immunoassays, which rely on quenching of fluorescence, when a quencher is brought into close proximity to the fluorescer due to binding of immunologically related materials.

In describing the subject invention, the simple monomeric spectroscopically active compounds used for conjugation will be considered first, followed by consideration of the various conjugates. The compounds are chemically stable, even at basic pHs, so that they maintain their spectroscopic properties during use.

The compounds employed for conjugation to other compounds will be characterized by having an active functionality which forms a stable covalent bond with another compound, usually an amide bond or thioether bond. For the most part, the linking functionality will involve a non-oxo-carbonyl, including the nitrogen and sulfur analogues thereof, and may be bonded directly to an annular carbon atom of the phenyl group of the fluorescein, bonded through a linking group, or bonded directly or through a linking group to the oxy- or thioether functionality. Various functionalities may be employed which are compatible with the other functionalities in the molecule. The functionalities include carboxylic acid, which may be activated with carbodiimide or activating alcohols to provide active ester groups, isocyanates, isothiocyanates, imidates or the like which groups react with amino functionalities to form amides, thioamides or amidines. Alternatively, one can have amino groups as the functionality, which can be combined with carboxylic acids or derivatives to provide amide links. Finally, one can employ mercapto functionalities, which can be combined with ethylenic groups, particularly activated ethylenic groups, such as maleic acid derivatives, or vice versa, to provide thioethers.

For the most part, a preferred group of compounds will have the following formula:

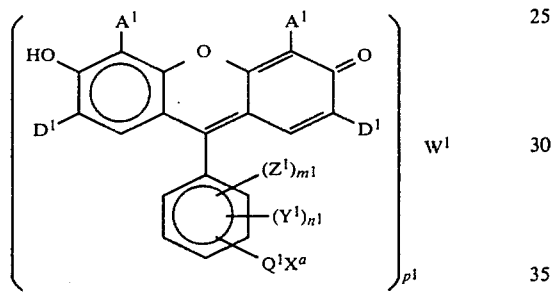

wherein:
the two $A^1$s are the same or different, usually being the same except when one is the functionality for linking;
the two $D^1$s are the same or different, usually being the same except when one is the functionality for linking;
either the $A^1$s or the $D^1$s are oxyethers of the formula $-OM^1X^b$, wherein $M^1$ is a saturated aliphatic hydrocarbylene group of from 1 to 6, usually 1 to 3 carbon atoms, preferably straight chain and of from 1 to 2 carbon atoms, i.e. methylene or ethylene (hydrocarbylene intends a divalent organic radical composed solely of carbon and hydrogen); when not oxyethers, the $A^1$s are preferably hydrogen or halo particularly of atomic number 9 to 53, more particularly chloro or iodo, and the $D^1$s are preferably hydrogen, halo, or alkyl of up to six carbon atom;
one of the $X^a$ or $X^b$s, usually $X^a$, is taken together with $W^1$ to form an active functionality, which may have the same definition as $-XW$, but will usually be a non-oxo-carbonyl containing functionality (including sulfur-thiono-analogs thereof), such as mixed anhydride, e.g. with butyl chloroformate, carboxylic acid, activated ester, isocyanate or isothiocyanate, with the proviso that $X^b$ when taken together with $W^1$ is a carboxylic acid or derivative thereof;
when not taken together with $W^1$, one of the $X^a$ or $X^b$s is a linking group to $W^1$ which is carbonyl, forming an amide or ester with $W^1$, carbamyl forming a urea with $W^1$, or thiocarbamyl forming a thiourea with $W^1$;
when not an active or linking functionality $X^a$ is hydrogen, or non-oxo-carbonyl e.g. carboxy, and $X^b$ is hydrogen or carboxyl, usually hydrogen;
$Q^1$ may be the same as Q, a bond or spacer arm, but will usually be a bond or spacer arm of from 1 to 12, usually 2 to 12 atoms in the chain which are carbon, nitrogen and oxygen, generally having from 1 to 10, usually 1 to 8 carbon atoms and 0 to 8 heteroatoms which are nitrogen, oxygen and sulfur, wherein oxygen is present bonded solely to carbon e.g. non-oxo-carbonyl or oxy ether, sulfur is analogous to oxygen and nitrogen is amido or bonded solely to carbon e.g. tertiary amino; $Q^1$ is usually a bond when $X^a$ is other than a reactive functionality or linking functionality;
when $W^1$ is not taken together with $X^a$ or $X^b$, $W^1$ is a ligand, receptor or support, usually having amino or hydroxyl, particularly amino functionalities for linking;
$p^1$ may be the same as p, being 1 when one of $X^a$ or $X^b$s are taken together with $W^1$, and is otherwise 1 to the molecular weight of $W^1$ divided by 500, usually divided by 1500, generally in the range of 1 to 200, usually in the range of 1 to 100 and more usually in the range of 1 to 50;
$Z^1$ is an acidic anionic group, such as a carboxylic acid or sulfonic acid;
$m^1$ is an integer of from 1 to 3;
$Y^1$ is halogen of atomic number 9 to 53, particularly chloro;
$n^1$ is an integer of from 0 to 3, wherein $m^1$ plus $n^1$ is not greater than 4;

The compounds will normally have from 0 to 6, usually 0 to 5 halogen of atomic number 9 to 53, preferably chlorine or iodine, and usually from 0 to 4 chlorines, frequently 2 to 4 chlorines. The compounds will normally have at least two carboxylic acid groups and up to 5 carboxylic acids groups, preferably having from 2 to 3 carboxylic acid groups. The non-oxo-carbonyl linking functionality may or may not be bonded to a carbon atom, but is preferably bonded to a carbon atom.

The preferred compounds having the active functionality will for the most part have the following formula:

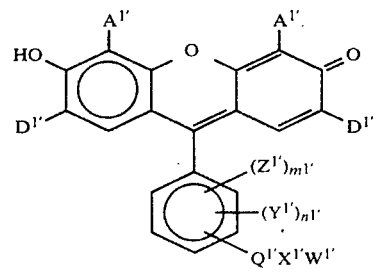

wherein:
either the $A^{1'}$s or $D^{1'}$s are alkoxy of from 1 to 3, usually 1 to 2 carbon atoms, when not alkoxy they are as previously described for As and Ds;
$Y^{1'}$, $Z^{1'}$, $m^{1'}$ and $n^{1'}$ have the same scope as the unprimed symbols;
$W^{1'}$ is an active functionality having a non-oxo-carbonyl group or sulfur analog (thiono) and includes acyl halides, mixed anhydrides and, activated ester, as well as isocyanate and isothiocyanate.

$Q^{1'}$ is a bond or spacer arm of from 1 to 12, usually 1 to 10 atoms in the chain which are carbon, nitrogen and oxygen, usually carbon and nitrogen, and has from about 1 to 12, usually 1 to 10 carbon atoms and 0 to 8, usually 0 to 6 heteroatoms which are nitrogen, oxygen and sulfur, particularly nitrogen and oxygen, wherein nitrogen is present as amido or bonded solely to carbon and the chalcogens (oxygen and sulfur) are bonded solely to carbon, doubly bonded (oxo and thiono) or singly bonded (oxy or thio); as a spacer arm $Q^{1'}$ can be alkylene of from 1 to 8, usually 1 to 4 carbon atoms, glycyl or polyglycyl of from 1 to 4 glycyl units where the final carboxy is $W^{1'}$, or the like;

The following is a list of compounds in this invention which find use for conjugating.

TABLE I

The compounds are substituted 9-phenyl-6-hydroxy-3H-xanthen-3-ones or when the compound is fluorescein having a 2-carboxy group, the compounds are 3',6'-dihydroxyspiro[isobenzofuran-(3H),9'-[9H]xanthen]-3-one. The numbering in this list is based on the former naming.

2,7-dimethoxy-9-(2',4'-dicarboxyphenyl)-6-hydroxy-3H-xanthen-3-one
2,7-diethoxy-9-(2',3',4'-tricarboxyphenyl)-6-hydroxy-3H-xanthen-3-one
2,7-diethoxy-9-(2',4',5'-tricarboxy-3',6'-dichlorophenyl)-6-hydroxy-3H-xanthen-3-one
2,7-dipropoxy-4,5-dichloro-9-(2',4'-dicarboxy-6-sulfonatophenyl)-6-hydroxy-3H-xanthen-3-one
2,7-dimethoxy-4,5-dibromo-9-(2',4',5'-tricarboxyphenyl)-6-hydroxy-3H-xanthen-3-one
2,7-dimethoxy-4,5-dichloro-9-(2',4',5'-tricarboxyphenyl)-6-hydroxy-3H-xanthen-3-one
2,7-dimethoxy-9-(3',4'-dicarboxyphenyl)-6-hydroxy-3H-xanthen-3-one
2,7-dimethoxy-9-(3',4'-dicarboxy-2',5',6'-trichlorophenyl)-6-hydroxy-3H-xanthen-3-one
2,7-(2'''-carboxyethoxy)-9-(2'-carboxyphenyl)-6-hydroxy-3H-xanthen-3-one
2,7-diethoxy-4,5-dibromo-9-(2',4',5'-tricarboxyphenyl)-6-hydroxy-3H-xanthen-3-one
2,7-dimethoxy-9-[2'-carboxy-4'-fluoro-5'-(N-carboxymethyl carboxamide)phenyl]-6-hydroxy-3H-xanthen-3-one
2,7-dimethoxy-9-(2',4'-dicarboxy-5'-aminophenyl)-6-hydroxy-3H-xanthen-3-one
2,7-dimethoxy-9-(2'-carboxy-4'-isothiocyanatophenyl)-6-hydroxy-3H-xanthen-3-one
2,7-diethoxy-9-(2'-carboxy-4'-mercaptophenyl)-6-hydroxy-3H-xanthen-3-one
2,7-dimethoxy-4,5-dibromo-9-(2'-carboxy-4'-mercaptomethylphenyl)-6-hydroxy-3H-xanthen-3-one
2,7-dimethoxy-4,5-dichloro-9-(2'-carboxy-4'-cyanophenyl)-6-hydroxy-3H-xanthen-3-one
4,5-dimethoxy-9-(2',4',5'-tricarboxy phenyl)-6-hydroxy-3H-xanthen-3-one
4,5-dimethoxy-9-(2',5'-dicarboxy phenyl)-6-hydroxy-3H-xanthen-3-one
4,5-dimethoxy-2,7-diiodo-9-(2',4',5'-tricarboxy phenyl)-6-hydroxy-3H-xanthen-3-one
4,5-dimethoxy-2,7-dichloro-9-(2',4',5'-tricarboxyphenyl)-6-hydroxy-3H-xanthen-3-one
4,5-dimethoxy-2,7-dichloro-9-(2',4',5'-tricarboxy-3',6'-dichlorophenyl)-6-hydroxy-3H-xanthen-3-one
4,5-di(2''-carboxyethoxy)-2,7-diiodo-9-(2'-carboxy-4'-sulfonatophenyl)-6-hydroxy-3H-xanthen-3-one
4,5-dipropoxy-2,7-dibromo-9-(2',4'-dicarboxy-3',5',6'-trichlorophenyl)-6-hydroxy-3H-xanthen-3-one
4,5-diethoxy-2,7-dichloro-9-(2'-carboxy-4'-amino-5'-sulfonatophenyl)-6-hydroxy-3H-xanthen-3-one
4,5-dimethoxy-2,7-diiodo-9-(2'-carboxy-4'-isothiocyanatophenyl)-6-hydroxy-3H-xanthen-3-one
4,5-diethoxy-2,7-diiodo-9-[2',4'-dicarboxy-5'-(N-carboxymethyl formamide)phenyl]-6-hydroxy-3H-xanthen-3-one
4,5-dimethoxy-2,7-dichloro-9-(2',4'-dicarboxy-3',5',6'-trichlorophenyl)-6-hydroxy-3H-xanthen-3-one
4,5-diethoxy-2,7-dichloro-9-(4',5'-dicarboxy-2',3',6'-trichlorophenyl)-6-hydroxy-3H-xanthen-3-one
4,5-dimethoxy-2,7-diiodo-9-(2'-carboxy-4'-mercaptomethylphenyl)-6-hydroxy-3H-xanthen-3-one The above list is intended to merely be illustrative and not exhaustive of the compounds included within the scope of the subject invention.

The compounds of this invention having active functionalities may be conjugated to ligands or supports having complementary heterofunctionalities. The following table indicates illustrative ligand functionalities, active functionalities for linking the compounds of this invention with the ligands and the resulting linking unit.

| Spectroscopic Compound Functionality* | Ligand Functionality | Linking Group |
|---|---|---|
| —CO—OH, —OT¹, —OCO₂T | NH₂ | —CO—NH— |
| —NCO | NH₂ | —NHCONH— |
| —NCS | NH₂ | —NHCSNH— |
| 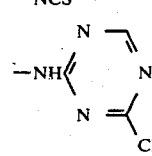 | NH₂ | 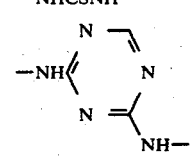 |
| —C=C—CO— | SH | 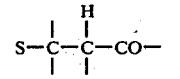 |
| —CHO | NH₂ | —CH₂NH— |
| —SO₂Cl | NH₂ | —SO₂NH— |
| —COCH₂halo | SH or OH | —COCH₂—S— or —O— |

*T is alkyl; T¹ is alkyl or electronegative ester activating group.

In most cases, the ligand functionality and spectroscopic compound functionality may be switched.

For the most part the ligand conjugates will have the following formula:

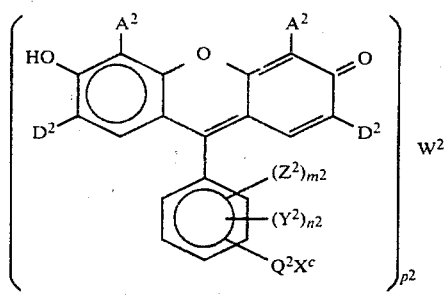

wherein:
- the $A^2$s are the same or different, normally being the same, except when the linking site;
- the $D^2$s are the same or different, normally being the same, except when the linking site;
- either the $A^2$s or $D^2$s are ethers, usually oxyethers, of the formula —$HM^2X^d$, wherein H is oxygen or sulfur, $M^2$ may be the same as M, but usually is an alkylene group of from 1 to 6, usually 1 to 3 carbon atoms, $X^d$ is carboxy or hydrogen, usually hydrogen; and when not ethers, as defined previously for As and Ds;
- $Y^2$, $Z^2$, $m^2$ and $n^2$ are the same as Y, Z, m and n respectively;
- $Q^2$ may be the same as Q, but will usually be the same as $Q^1$;
- $X^c$ may come within the same definition as X, treating $W^2$ as W, but will usually be a non-oxo-carbonyl containing functionality, including nitrogen and sulfur analogs, such as carbonyl, imido, carbamyl and thiocarbamyl to form respectively amide, amidine, urea and thiourea, when combined with amino on the ligand;
- $p^2$ is 1 to the molecular weight of $W^2$ divided by 500, usually 1000, more usually 2000; with haptenic ligands of from about 125 to 2000 molecular weight, $p^2$ will usually be 1; with antigenic ligands of greater than 2000 molecular weight, usually greater than 5000 molecular weight, $p^2$ will generally be on the average from about 1 to 200, usually 1 to 100 and more usually 2 to 50; and
- $W^2$ is a ligand, receptor or support, as a ligand $W^2$ will be haptenic or antigenic; haptenic ligands will generally be from about 125 to 2000 molecular weight and will have at least one polar functionality, which may or may not be the site for linking; antigenic ligands will be polyepitopic, will usually be poly(amino acids), nucleic acids, polysaccharides and combinations thereof, generally of at least 2000, usually at least 5000 molecular weight and may be 10 million or more molecular weight; supports may be of indeterminate molecular weight, usually at least 10,000, more usually at least 20,000 molecular weight and may be 10 million or more, with soluble supports generally under 10 million molecular weight; the supports may be naturally occurring or synthetic, may be particulate or have a shaped form; swellable or non-swellable by aqueous media; the support may be cross-linked or non-cross-linked, may be a single substance or a mixture of substances; naturally occurring supports may include polysaccharides, nucleic acids, poly(amino acids) e.g. polypeptides and proteins, rubbers, lignin, vesicles, combinations thereof, and the like; synthetic supports may include addition and condensation polymers e.g. polystyrene, polyacrylics, vinyl compounds, polyesters, polyethers and polyamides; charcoal, metal chalcogenides, glass, liposomes, and the like.

A preferred group of ligand conjugates will have the following formula:

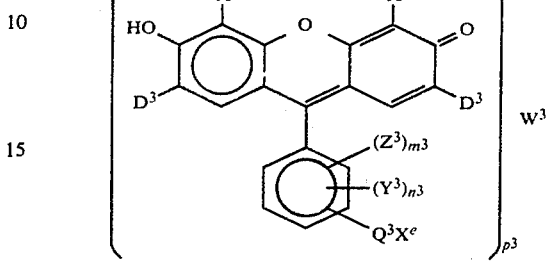

wherein:
- for quencher molecules, the $A^3$s are alkoxy of from 1 to 2 carbon atoms and the $D^3$s are hydrogen or halo, particularly chloro, bromo or iodo, or alkyl of from 1 to 6 carbon atoms;
- for fluorescer molecules, the $D^3$s are alkoxy of 1 to 2 carbon atoms and the $A^3$s are hydrogen or halo, particularly chloro or bromo;
- $Z^3$ is carboxyl;
- $Y^3$ is halo, particularly chloro;
- $Q^3$ is a bond or spacer arm of from 1 to 9, usually 2 to 9 atoms in the chain, which are carbon and nitrogen, particularly amido nitrogen, wherein the spacer arm is composed solely of carbon, oxygen, nitrogen and hydrogen, wherein oxygen is bonded solely to carbon and is oxy or oxo, particularly non-oxo-carbonyl; useful spacer arms include alkylene of from 1 to 6, usually 2 to 4 carbon atoms, mono- or poly-amidomethylene (—$CONHCH_2$—) aminomono- or amino poly-amidomethylene (—$HN(CONHCH_2)_x$), or aminothiono mono- or poly(aminomethylenecarbonyl) amino-methylene (—$NHCS(NHCH_2CO)_x NHCH_2$—), wherein x is 1 to 3;
- $X^e$ is non-oxo-carbonyl, carbamyl or thiocarbamyl, bonded to amino of $W^3$ to form an amide bond;
- $W^3$ is a receptor or ligand, usually haptenic of from about 125 to 1000 molecular weight or antigen of from about 2000 to 10 million, usually 5000 to 2,000,000, more usually 5000 to 1,000,000 molecular weight; $W^2$ is particularly a poly(amino acid) or polysaccharide antigen and may be any hapten;
- $p^3$ is 1 to the molecular weight of $W^3$ divided by 500, usually divided by about 2000, generally in the range of about 1 to 200, more usually in the range of about 2 to 150, and frequently in the range of about 1 to 75. For ligands below 500,000 molecular weight $p^3$ will generally be in the range of about 2 to 50;
- $m^3$ is an integer of from 1 to 2;
- $n^3$ is an integer of from 0 to 3, with $m^3$ plus $n^3$ not greater than 4.

In some instances it may be desirable to have the conjugate of the ligand and subject fluorescer bound, either covalently or non-covalently to a support. The binding of the conjugate to a support may be by means of a covalent bond to a functionality either on the ligand or subject fluorescer or by non-covalent binding between the ligand, normally polyepitopic, and a receptor, usually an antibody, which in turn may be covalently or non-covalently bound to the support. The ligand-fluorescer conjugates bound to a support will for the most part have the following formula:

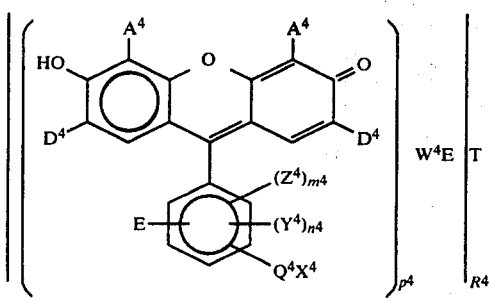

wherein:
the two $A^4$s are the same or different, normally being the same except when one is the linking functionality, the two $D^4$s are the same or different, normally being the same except when one is the linking functionality;

either the $A^4$s or $D^4$s are ethers of the formula —$JM^4X^4$, wherein J is oxygen or sulfur, usually oxygen; when other than —$JM^4X^4$, the $A^4$s and $D^4$s are as described previously for As and Ds;

$M^4$ is a divalent hydrocarbon group, normally saturated aliphatic, of from 1 to 8, usually 1 to 6 and preferably 1 to 3 carbon atoms, usually straight chain;

one of the $X^4$s is a linking functionality to a ligand and is usually non-oxo-carbonyl (including the nitrogen and sulfur analogs thereof) having one valence to carbon, carbamyl, thiocarbamyl, imido, thioether, alkylamino, thio- or oxyacetyl, with the proviso that $X^4$ as the linking group is non-oxo-carbonyl when bonded to $M^4$; when an $X^4$ is not a linking functionality the $X^4$ bonded to $M^4$ is hydrogen or non-oxo-carbonyl and the $X^4$ bonded to $Q^4$ is hydrogen, non-oxo-carbonyl or halo, wherein $Q^4$ will be a bond;

$Q^4$ is a bond or spacer arm, usually aliphatic, aromatic, heterocyclic, or combination thereof, having from about 1 to 16, usually 1 to 12, more usually 1 to 8 atoms in the chain, which are carbon, nitrogen, oxygen and sulfur, wherein the nitrogen is amido or amino, as amino, usually tert-amino, oxygen is oxy and sulfur is thioether, with the chalcogen bonded solely to carbon and heteroatoms being separated by at least two carbon atoms when bonded to saturated carbon atoms; the total number of carbon atoms being about 1 to 20, usually about 1 to 12, with the total number of heteroatoms being 0 to 10, usually 0 to 8, with oxygen as oxy or non-oxo-carbonyl, there being from 0 to 9, usually 0 to 4 heterofunctionalities, such as amido, amino and oxy;

$Z^4$ is an anionic group, such as a carboxylic acid or sulfonic acid;

$Y^4$ is halogen of atomic number 9 to 53, usually chloro;

$m^4$ is an integer of from 0 to 3, usually 1 to 3;

$n^4$ is an integer of from 0 to 4, wherein the sum of $m^4$ plus $n^4$ is not greater than 4;

$p^4$ is equal to the molecular weight of $W^4$ divided by 500, usually divided by 1,000 and more usually divided by 1,500, generally ranging from 1 to 200, usually from 1 to 100, more usually from 1 to 50;

$W^4$ is a receptor or ligand, generally of at least about 125 molecular weight, which may be haptenic or antigenic, haptenic ligands usually being from about 125 to 2,000 molecular weight, and antigenic ligands and receptors being from about 5,000 to $1 \times 10^7$ molecular weight, the linkage generally being by amino, thio or oxy groups of the ligand;

one of the Es is a linking group, and when not a linking group, has no significance; when $W^4$ is a hapten, the E bonded to the phenyl will normally be the linking group, while when $W^4$ is antigenic, the E bonded to $W^4$ will usually be the linking group; E will have the same limits as $X^4$, but will preferably be non-oxo-carbonyl, amino or thioether;

T is a support either soluble or insoluble and has previously been described in relation to W; and $r^4$ is at least one and up to the molecular weight of T divided by 500, usually divided by 1,000, and more usually divided by 1,500.

When the nine position of the xanthene ring has an aliphatic substituent, for the most part the compounds will have the following formula:

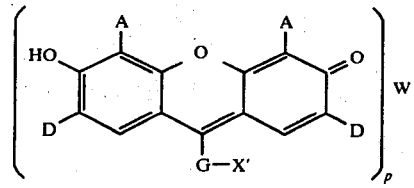

wherein
the A's and D's have been defined previously, wherein —OMX is the same as —OMX';

G is a saturated hydrocarbon group of from 2 to 7 carbon atoms having 0 to 5 to 7 annular members;

X' comes within the definition of X, but will normally be non-oxo-carboxyl, and when taken together with W, particularly carboxy; and W and p have the same definitions as previously indicated.

For use in immunoassays or in other diagnostic situations, the spectroscopically active compounds of this invention will be conjugated to a compound of interest, including a receptor for an analyte or a ligand. (By receptor is intended any compound which specifically bonds to a particular spatial and polar molecular organization and a ligand is an organic molecule having such organization.) The analyte will normally be haptenic or antigenic. Where these compounds do not have available functionalities for linking, they will be modified to introduce such a functionality, while still retaining the receptor recognition properties in the resulting product. These compounds which are analogues of the analyte, which analyte may also be referred to as a ligand, will be referred to as ligand analogues.

As indicated previously, the compounds of this invention may be conjugated to compounds which may be measured by known immunoassay techniques. The resulting conjugates are reagents which compete in an assay medium with the compound of interest or analyte in a sample. Therefore, the conjugate retains a sufficient proportion of the structure of the compound of interest to be able to compete with the compound of interest for receptor, usually an antibody.

The analytes or their analogues, receptors or ligands, which are conjugated to the spectroscopically active compounds of this invention are characterized by being monoepitopic or polyepitopic.

Analyte

The ligand analytes of this invention are characterized by being monoepitopic or polyepitopic. The polyepitopic ligand analytes will normally be poly(amino acids) i.e. polypeptides and proteins, polysaccharides, nucleic acids, and combinations thereof. Such combinations of assemblages include bacteria, viruses, chromosomes, genes, mitochondria, nuclei, cell membranes, and the like.

For the most part, the polyepitopic ligand analytes employed in the subject invention will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

The wide variety of proteins may be considered as to the family of proteins having similar structural features, proteins having particular biological functions, proteins related to specific microorganisms, particularly disease causing microorganisms, etc.

The following are classes of proteins related by structure:

protamines
histones
albumins
globulins
scleroproteins
phosphoproteins
mucoproteins
chromoproteins
lipoproteins
nucleoproteins
glycoproteins
proteoglycans
unclassified proteins, e.g. somatotropin, prolactin, insulin, pepsin A number of proteins found in the human plasma are important clinically and include:

Prealbumin
Albumin
$\alpha_1$-Lipoprotein
$\alpha_1$-Acid glycoprotein
$\alpha_1$-Antitrypsin
$\alpha_1$-Glycoprotein
Transcortin
4.6S-Postalbumin
Tryptophan-poor
 $\alpha_1$-glycoprotein
$\alpha_1$X-Glycoprotein
Thyroxin-binding globulin
Inter-$\alpha$-trypsin-inhibitor
Gc-globulin
 (Gc 1-1)
 (Gc 2-1)
 (Gc 2-2)
Haptoglobin
 (Hp 1-1)
 (Hp 2-1)
 (Hp 2-2)
Ceruloplasmin
Cholinesterase
$\alpha_2$-Lipoprotein(s)
Myoglobin
C-Reactive Protein
$\alpha_2$-Macroglobulin
$\alpha_2$-HS-glycoprotein
Zn-$\alpha_2$-glycoprotein
$\alpha_2$-Neuramino-glycoprotein
Erythropoietin
$\beta$-lipoprotein
Transferrin
Hemopexin
Fibrinogen
Plasminogen
$\beta_2$-glycoprotein I
$\beta_2$-glycoprotein II
Immunoglobulin G
 (IgG) or $\gamma$G-globulin
Mol. formula:
 $\gamma_2\kappa_2$ or $\gamma_2\lambda_2$
Immunoglobulin A (IgA)
 or $\gamma$A-globulin
Mol. formula:
 $(\alpha_2\kappa_2)^n$ or $(\alpha_2\lambda_2)^n$
Immunoglobulin M
 (IgM) or $\gamma$M-globulin
Mol. formula:
 $(\mu_2\kappa_2)^5$ or $(\mu_2\lambda_2)^5$
Immunoglobulin D(IgD)
 or $\gamma$D-Globulin ($\gamma$D)
Mol. formula:
 $(\delta_2\kappa_2)$ or $\delta_2\lambda_2$)
Immunoglobulin E (IgE)
 or $\gamma$E-Globulin ($\gamma$E)
Mol. formula:
 $(\epsilon_2\kappa_2)$ or $(\epsilon_2\lambda_2)$
Free $\kappa$ and $\lambda$ light chains
Complement factors:
C'1
 C'1q
 C'1r
 C'1s
C'2
C'3
 $\beta_1$A
 $\alpha_2$D
C'4
C'5
C'6
C'7
C'8
C'9

Important blood clotting factors include:

| BLOOD CLOTTING FACTORS | |
|---|---|
| International designation | Name |
| I | Fibrinogen |
| II | Prothrombin |
| IIa | Thrombin |
| III | Tissue thromboplastin |
| V and VI | Proaccelerin, accelerator globulin |

-continued
BLOOD CLOTTING FACTORS

| International designation | Name |
| --- | --- |
| VII | Proconvertin |
| VIII | Antihemophilic globulin (AHG) |
| IX | Christmas factor, plasma thromboplastin component (PTC) |
| X | Stuart-Prower factor, autoprothrombin III |
| XI | Plasma thromboplastin antecedent (PTA) |
| XII | Hagemann factor |
| XIII | Fibrin-stabilizing factor |

Important protein hormones include:

Peptide and Protein Hormones

Parathyroid hormone
  (parathromone)
Thyrocalcitonin
Insulin
Glucagon
Relaxin
Erythropoietin
Melanotropin
  (melanocyte-stimulating hormone; intermedin)
Somatotropin
  (growth hormone)
Corticotropin
  (adrenocorticotropic hormone)
Thyrotropin
Follicle-stimulating hormone
Luteinizing hormone
  (interstitial cell-stimulating hormone)
Luteomammotropic hormone
  (luteotropin, prolactin)
Gonadotropin
  (chlorionic gonadotropin)

Tissue Hormones

Secretin
Gastrin
Angiotensin I and II
Bradykinin
Human placental lactogen

Peptide Hormones from the Neurohypophysis

Oxytocin
Vasopressin
Releasing factors (RF)
  CRF, LRF, TRF, Somatotropin-RF, GRF, FSH-RF, PIF, MIF Other polymeric materials of interest are mucopolysaccharides and polysaccharides.

Illustrative antigenic polysaccharides derived from microorganisms are as follows:

| Species of Microorganisms | Hemosensitin Found in |
| --- | --- |
| Streptococcus pyogenes | Polysaccharide |
| Diplococcus pneumoniae | Polysaccharide |
| Neisseria meningitidis | Polysaccharide |
| Neisseria gonorrheae | Polysaccharide |
| Corynebacterium diphtheriae | Polysaccharide |
| Actinobacillus mallei; Actinobacillus whitemori | Crude extract |
| Francisella tularensis | Lipopolysaccharide |
| Pasteurella pestis | Polysaccharide |
| Pasteurella pestis | Polysaccharide |
| Pasteurella multocida | Capsular antigen |
| Brucella abortus | Crude extract |
| Haemophilus influenzae | Polysaccharide |
| Haemophilus pertussis | Crude |
| Treponema reiteri | Polysaccharide |
| Veillonella | Lipopolysaccharide |
| Erysipelothrix | Polysaccharide |
| Listeria monocytogenes | Polysaccharide |
| Chromobacterium | Lipopolysaccharide |
| Mycobacterium tuberculosis | Saline extract of 90% phenol extracted mycobacteria and polysaccharide fraction of cells and tuberculin |
| Klebsiella aerogenes | Polysaccharide |
| Klebsiella cloacae | Polysaccharide |
| Salmonella typhosa | Lipopolysaccharide, Polysaccharide |
| Salmonella typhi-murium; Salmonella derby Salmonella pullorum | Polysaccharide |
| Shigella dysenteriae | Polysaccharide |
| Shigella flexneri | |
| Shigella sonnei | Crude, Polysaccharide |
| Rickettsiae | Crude extract |
| Candida albicans | Polysaccharide |
| Entamoeba histolytica | Crude extract |

The microorganisms which are assayed may be intact, lysed, ground or otherwise fragmented, and the resulting composition or portion, e.g. by extraction, assayed. Microorganisms of interest include:

Corynebacteria
  Corynebacterium diptheriae
Pneumococci
  Diplococcus pheumoniae
Streptococci
  Streptococcus pyogenes
  Streptococcus salivarus
Staphylococci
  Staphylococcus aureus
  Staphylococcus albus
Neisseriae
  Neisseria meningitidis
  Neisseria gonorrheae
Enterobacteriaciae
  Esherichia coli          ⎫
  Aerobacter aerogenes     ⎬ The coliform bacteria
  Klebsiella pneumoniae    ⎭
  Salmonella typhosa       ⎫
  Salmonella choleraesuis  ⎬ The Salmonellae
  Salmonella typhimurium   ⎭
  Shigella dysenteriae     ⎫
  Shigella schmitzii       ⎪
  Shigella arabinotarda    ⎪
  Shigella flexneri        ⎬ The Shigellae
  Shigella boydii          ⎪
  Shigella Sonnei          ⎭
Other enteric bacilli
  Proteus vulgaris         ⎫
  Proteus mirabilis        ⎬ Proteus species
  Proteus morgani          ⎭
  Pseudomonas aeruginosa
  Alcaligenes faecalis -continued Vibrio cholerae
Hemophilus-Bordetella group
Hemophilus influenzae,     H. ducreyi
    H. hemophilus
    H. aegypticus
    H. parainfluenzae
Bordetella pertussis
Pasteurellae
Pasteurella pestis
Pasteurella tulareusis
Brucellae
Brucella melitensis
Brucella abortus
Brucella suis
Aerobic Spore-forming Bacilli
Bacillus anthracis
Bacillus subtilis
Bacillus megaterium
Bacillus cereus
Anaerobic Spore-forming Bacilli
Clostridium botulinum
Clostridium tetani
Clostridium perfringens
Clostridium novyi
Clostridium septicum
Clostridium histolyticum
Clostridium tertium
Clostridium bifermentans
Clostridium sporogenes
Mycobacteria
Mycobacterium tuberculosis hominis
Mycobacterium bovis
Mycobacterium avium
Mycobacterium leprae
Mycobacterium paratuberculosis
Actinomycetes (fungus-like bacteria)
Actinomyces israelii
Actinomyces bovis
Actinomyces naeslundii
Nocardia asteroides
Nocardia brasiliensis
The Spirochetes
Treponema pallidum     Spirillum minus
Treponema pertenue     Streptobacillus moniliformis
Treponema carateum
Borrelia recurrentis
Leptospira icterohemorrhagiae
Leptospira canicola
Mycoplasmas
Mycoplasma pneumoniae
Other pathogens
Listeria monocytogenes
Erysipelothrix rhusiopathiae
Streptobacillus moniliformis
Donvania granulomatis
Bartonella bacilliformis
Rickettsiae (bacteria-like parasites)
Rickettsia prowazekii
Rickettsia mooseri
Rickettsia rickettsii
Rickettsia conori
Rickettsia australis
Rickettsia sibiricus
Rickettsia akari
Rickettsia tsutsugamusgi
Rickettsia burnetii
Rickettsia quintana
Chlamydia
(unclassifiable parasites bacterial/viral)
Chlamydia agents (naming uncertain)
Fungi
Cryptococcus neoformans
Blastomyces dermatidis
Histoplasma capsulatum
Coccidioides immitis
Paracoccidioides brasiliensis
Candida albicans
Aspergillus fumigatus -continued Mucor corymbifer (Absida corymbifera)
Rhizopus oryzae
Rhizopus arrhizus         ⎫
Rhizopus nigricans        ⎬ Phycomycetes
Sporotrichum schenkii     ⎭
Fonsecaea pedrosoi
Fonsecaea compacta
Fonsecaea dermatidis
Cladosporium carrionii
Phialophora verrucosa
Aspergillus nidulans
Madurella mycetomi
Madurella grisea
Allescheria boydii
Phialosphora jeanselmei
Microsporum gupseum
Trichophyton mentagrophytes
Keratinomyces ajelloi
Microsporum canis
Trichophyton rubrum
Microsporum andouini
Viruses
Adenoviruses
Herpes Viruses
Herpes simplex
Varicella (Chicken pox)
Herpes Zoster (Shingles)
Virus B
Cytomegalovirus
Pox Viruses
Variola (smallpox)
Vaccinia
Poxvirus bovis
Paravaccinia
Molluscum contagiusum
Picornaviruses
Poliovirus
Coxsackievirus
Echoviruses
Rhinoviruses
Myxoviruses
Influenza (A, B, and C)
Parainfluenza (1-14)
Mumps Virus
Newcastle Disease Virus
Measles Virus
Rinderpest Virus
Canine Distemper Virus
Respiratory Syncytial Virus
Rubella Virus
Arboviruses
Eastern Equine Eucephalitis Virus
Wester Equine Eucephalitis Virus
Sindbis Virus
Chikugunya Virus
Semliki Forest Virus
Mayora Virus
St. Louis Encephalitis Virus
California Encephalitis Virus
Colorado Tick Fever Virus
Yellow Fever Virus
Dengue Virus
Reoviruses
Reovirus Types 1-3
Hepatitia
Hepatitia A Virus
Hepatitis B Virus
Tumor Viruses
Rauscher Leukemia Virus
Gross Virus
Maloney Leukemia Virus The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which includes cocaine and benzoyl ecgonine, their derivatives and metabolites; ergot alkaloids, which includes the diethylamide of lysergic acid; steroid alkaloids; iminazolyl alkaloids; quinazoline alkaloids, isoquinoline alkaloids; quinoline alkaloids; which includes quinine and quinidine; diterpene alkaloids; their derivatives and metabolites.

The next group of drugs includes steroids, which includes the estrogens, gestogens, androgens, andrenocortical steroids, bile acids, cardiotonic glycosides and aglycones, which includes digoxin and digoxigenin, saponins and sapogenins, their derivatives and metabolites. Also included are the steriod mimetic substances, such as diethylstilbestrol.

The next group of drugs is lactams having from 5 to 6 annular members, which include the barbiturates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, their metabolites.

The next group of drugs is aminoalkylbenzenes, with alkyl of from 2 to 3 carbon atoms, which includes ephedrine, L-dopa, epinephrine, narceine, papverine, their metabolites and derivatives.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g $B_{12}$, C, D, E and K, folic acid, thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, their metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, their metabolites and derivatives.

The next group of compounds is amino acids and small peptides which include polyiodothyronines e.g. thyroxine, and triiodothyronine, oxytocin, ACTH, angiotensin, met- and leu-enkephalin their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

Receptors are compounds capable of binding to a particular spacial and polar organization of a molecule. For the most part, receptors are antibodies, particularly IgG, IgA, IgE and IgM. The receptors may be analytes or may be employed as reagents in immunoassay. In either event, the receptors can be conjugated to the spectroscopically active compounds of this invention.

For receptor analytes, the molecular weights will generally range from 10,000 to $2 \times 10^6$, more usually from 10,000 to $10^6$. For immunoglobulins, IgA, IgG, IgE and IgM, the molecular weights will generally vary from about 160,000 to about $10^6$. Enzymes will normally range from about 10,000 to 600,000 in molecular weight. Natural receptors vary widely, generally being at least about 25,000 molecular weight and may be $10^6$ or higher molecular weight, including such materials as avidin, thyroxine binding globulin, thyroxine binding prealbumin, transcortin, etc.

The compounds of the subject invention can be conjugated to a wide variety of ligands, haptens and antigens, and receptors to provide conjugates which are used in various assays, particularly immunoassays. Particular conjugates are of interest, because of the greater interest in the analyte as a drug, for example, the ease of quantitation with the compounds of the subject invention, or the like. The following are formulas of conjugates of particular interest.

The first conjugate of interest is a lactamchromophore conjugate of the formula

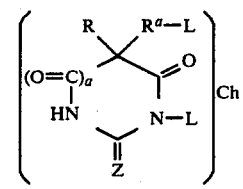

wherein:
- a is 1, except when R and $R^a$ are phenyl, when it is 0 or 1,
- Z is chalcogen, oxygen or sulfur, normally being oxygen;
- R and $R^a$ are hydrocarbon of from 1 to 7 carbon atoms, more usually of from 1 to 6 carbon atoms having from 0 to 1 site of ethylenic unsaturation when other than aromatic e.g. methyl, ethyl, sec-butyl, n-butyl, α-methylbutyl, isoamyl, hexyl, $\Delta^1$-cyclohexenyl and phenyl, particularly combinations of alkyl and α-methylbutyl or ethyl and phenyl, when a is 1, and two phenyls, when a is 0;
- one of the L's is a bond, or a functionality or group for linking to Ch, usually ending in oxy, amino, non-oxo-carbonyl or mercapto and having a chain of from 0 to 6, usually 0 to 4 carbon atoms; when other than the linking site, L is hydrogen;
- CH is of the formula:

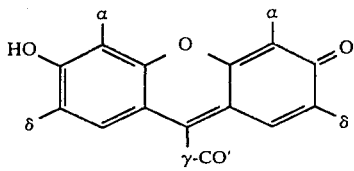

wherein:

α, δ and γ have been defined previously and CO' is an appropriate functionality for bonding to L to form an amide, amidine, urea, thiourea, ester, oxy- or thioether, or sec-amino functionality linking the ligand and chromophore; included in the above formula are all the preceding formulas of narrower scope, where an X is the linking functionality.

The next chromophore ligand conjugates of interest are for theophylline which will have the following formula:

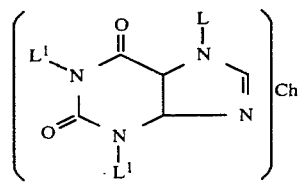

wherein:

one of L and $L^1$ is a bond or a functionality or group for linking to Ch, usually ending in oxy, amino, non-oxo-carbonyl or mercapto and having a chain of from 0 to 6, usually 0 to 4 carbon atoms; when other than the linking site, L is hydrogen and $L^1$ is methyl; and Ch has been defined previously.

The next chromophore ligand conjugates of interest are for aminoglycosides, particularly antimicrobial aminoglycosides, which for the most part will have the following formula:

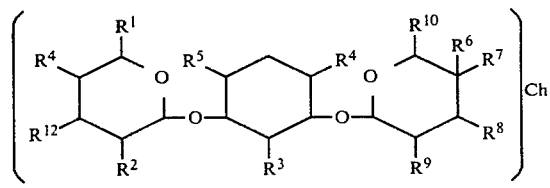

wherein:

L may be bonded to any one of the R groups; otherwise:

$R^2$ is amino(—$NH_2$), except for kanamycin and amikacin, when it is hydroxyl;

$R^3$, $R^7$ and $R^9$ are hydroxyl;

$R^4$ and $R^5$ are amino except for amikacin, where $R^4$ is 2-hydroxy-4-aminobutylamido;

$R^6$ is hydrogen or methyl, being methyl when gentamicin and hydrogen when tobramycin, kanamycin or amikacin;

$R^8$ is amino or methylamino, being methylamino when gentamicin and amino otherwise;

$R^{10}$ is hydrogen or hydroxymethyl, being hydrogen for gentamicin and hydroxymethyl otherwise;

$R^{11}$ and $R^{12}$ are hydrogen or hydroxyl, being hydrogen for gentamicin, hydroxyl for kanamycin and amikacin, and $R^{11}$ is hydroxyl and $R^{12}$ is hydrogen for tobramycin; and L and Ch have been defined previously.

The next chromophore ligand conjugates of interest are for tricyclic antidepressant drugs, which will have the following formula:

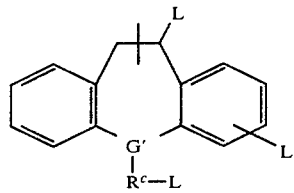

wherein:

one of the L's is a linking group as previously defined, and is otherwise hydrogen;

G' is N—, C= or CH—, the remaining two valences to the adjacent annular carbon atoms;

$R^c$ is a single or double bond joining L to G, or is aminopropyl or -ylidene having from 0 to 2 methyl groups bonded to the nitrogen.

The next chromophore ligand conjugates of interest are for benzodiazepines, which will have the following formula:

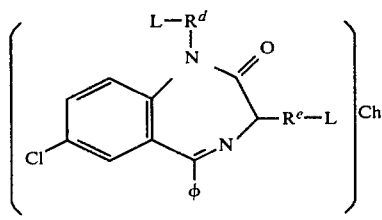

wherein:

L and Ch have been defined previously;

$R^d$ is a bond or methylene when L is hydrogen;

$R^e$ is a bond or oxy; and

φ is phenyl having from 0 to 1 ortho halogen of atomic number 9 to 17.

The linking group symbolized by L will vary depending upon the nature of R to which L is attached, and the group to which L is bonded. As indicated previously, L can be a bond, a functionality or a linking group terminating in a functionality capable of forming a covalent bond with a functionality present on Ch. When L is a bond, it will normally join a carbon atom to a heteroatom, particularly nitrogen and oxygen. When L is a heterofunctionality, it will normally be bonded to carbon, and will usually be oxy, thio, amino or non-oxo-carbonyl. When L is a linking group, it will normally have a chain of from 1 to 8, usually 1 to 6, more usually 1 to 4, of which 0 to 2, usually 0 to 1 are heteroatoms, which are oxygen, sulfur and nitrogen, the chalcogen being bonded solely to carbon, and the nitrogen being bonded solely to carbon and hydrogen, the chain terminating as methylene or with a heterofunctionality (as defined above for L), L having a total of 1 to 10, usually 1 to 6 carbon atoms and 0 to 4, usually 1 to 3 heteroatoms, which are oxygen, sulfur and nitrogen, the chalcogens usually being ethers or non-oxo-carbonyl and the nitrogen being amino or amido.

The subject conjugates can be used in a variety of ways for determining, qualitatively, semi-quantitatively, or quantitatively the presence of a compound of interest in a sample. Where compounds are to be detected in physiological fluids, the fluid may include serum, urine, saliva, lymph or the like. Where the compound of interest is involved in chemical processing or ecological concerns, the sample may involve an aqueous medium, an organic medium, soil, inorganic mixtures, or the like.

The assays will normally involve a change of spectroscopic properties due to a change of environment about the spectroscopically active compound or the bringing together of a fluorescer-quencher pair within sufficient proximity for the quencher to interact with the fluorescer.

In a first assay, steric exclusion is involved, in that receptors or antibodies for the ligand and for the fluorescer are employed, where simultaneous binding of the receptor for the ligand and receptor for the fluorescer is inhibited. Furthermore, when the receptor for the fluorescer (antifluorescer) is bound to the fluorescer, the fluorescence of the fluorescer is substantially diminished. Further reduction if not complete inhibition of fluorescence can be achieved by conjugation of quencher to the antifluorescer. This assay is extensively described in U.S. Pat. No. 3,998,943, issued Dec. 21, 1976. The fluorescein which is employed there may be substituted with the fluorescent compounds of the subject invention. The assay is described in columns 3 to 5 of the subject patent, which description is incorporated herein by reference.

Generally, the method involves combining the sample suspected of containing the analyte, the conjugate of the ligand and fluorescer, antifluorescer, and receptor for ligand or antiligand, when ligand is the analyte. The materials are combined in an aqueous medium at a pH in the range of 5 to 10, usually in the range of 6 to 9, at a temperature in the range of about 10° to 45° C., and the fluorescence determined either as a rate or equilibrium mode, readings being taken within about 1 second to one hour after all materials have been combined for a rate mode, while for an equilibrium mode, readings may be taken for as long as up to about 24 hours or longer.

In the next immunoassay technique, a fluorescer-quencher pair is employed, where one of the members of the pair is conjugated to a member of a specific binding pair, ligand and antiligand, and the other chromophor member is bound to the same or different member of the specific binding pair. For example, the fluorescer may be bound to antiligand and the quencher may be bound to different molecules of antiligand, so that when the two conjugated antiligands are brought together with antigen, the fluorescer and quencher are brought within quenching distance. Alternatively, one could bond one of the chromophors to the ligand and the other chromophor to the antiligand. This assay is extensively described in U.S. Pat. No. 3,996,345. The assay technique is described beginning with column 17 and ending at column 23, which description is incorporated herein by reference. The ratios of chromophor to ligand and receptor is described in columns 4 to 6, which description is incorporated herein by reference.

The assay is carried out substantially in the same manner as described above, except that in this assay, the fluorescer conjugate and quencher conjugate are added in conjunction with the sample and the fluorescence determined in comparison to an assay medium having a known amount of the analyte.

Other techniques may also be employed with the subject compounds, such as techniques involving heavy atom quenching as described in co-pending application Ser. No. 824,576, filed Aug. 13, 1977, now abandoned, or other assay techniques where a fluorescent molecule is desired which emits light at a wavelength substantially above the light emitted by fluorescent compounds naturally present in physiological fluids or other samples to be analyzed.

EXPERIMENTAL

The following examples are offered by way of illustration and not by way of limitation.

(All temperatures not otherwise indicated are centigrade. All parts and percents not otherwise indicated are by weight, except for mixtures of liquids, which are by volume. The following abbreviations are employed: THF-tetrahydrofuran; NHS-N-hydroxy succinimide; DMF-N,N-dimethyl formamide; DCC-dicyclohexyl carbodiimide; PEG-polyethylene glycol 6000.)

Ex. 1. Preparation of 2-chloro-4-methoxyresorcinol

Into a reaction flask was introduced 2 g of 2-chloro-3-hydroxy-4-methoxybenzaldehyde in 50 ml methylene dichloride with an excess of m-chloroperbenzoic acid and the reaction refluxed for 2.5 hrs. After removal of the solvent, the solid residue was dissolved in 10 ml methanol and stirred with approximately 10 weight percent aqueous sodium hydroxide (10 ml) for 1 hr. After acidification to pH 1 with dilute HCl, the solution was filtered and the precipitate washed with 10 ml of cold water. The combined filtrate and wash was extracted with ether, the ether washed with 5% NaHCO$_3$ (2×10 ml) and saturated NaCl solution (1×10 ml) and then evaporated to leave a solid which was crystallized from ethyl acetate-hexane mixture to provide the product as white silky needles (1.35 g). mp 69°–70°.

Ex. 2. Preparation of 3',6'-dihydroxy-4',5'-dichloro-2',7'-dimethoxyspiro[isobenzofuran-1(3H),9'-[9H]xanthen]-5 or 6-carboxy-3-one A mixture of the product of Example 1 (200 mg) and 100 mg of 1,2,4-benzenetricarboxylic anhydride was heated with 15 mg zinc chloride at 180°–85° for 30 min. The resulting red mixture was dissolved in 5% aqueous sodium hydroxide and precipitated with dilute HCl to pH 1. The precipitate was then chromatographed using CH$_2$Cl$_2$:MeOH:AcOH-9:1:0.05.

Ex. 3. Preparation of 3',6'-dihydroxy-4',5'-dimethoxyspiro[isobenzofuran-1(3H),9'-[9H]xanthen]-5 or 6-carboxy-3-one A mixture of pyrogallol-2-methyl ether (4 g) and 1,2,4-benzene tricarboxylic anhydride (2.3 g) was heated in an open test tube in a preheated oil bath at 190°–195° (outside oil bath temperature) for 3 hrs. A dark red mass was obtained. It was cooled and dissolved in 5% NaOH (35 ml), and acidified with concentrated HCl to pH 1. A dark red oil separated out. The solution was saturated with solid NaCl and stirred in the cold room overnight. The thick black tarry mass was separated and this tar macerated with saturated NaCl solution (2×15 ml). TLC (CH$_2$Cl$_2$:MeOH:AcOH 85:15:1) examination of the tar indicated the presence of a red spot and a few other spots having lower Rf. This tar was absorbed on 5 g of RP-2 silica gel 60 silanised (E. Marck Cat. No. 7719) and purified by a regular gravity column using RP-2 silica gel (35 g) prepared in CH$_2$Cl$_2$:methanol (100:0.25). The elution was carried out with the same solvent CH$_2$Cl$_2$:methanol (100:0.25). Elution was followed by TLC. The fractions containing the same red spots were combined and the solvent removed to give a red residue which was macerated with 20 ml of a mixture of CCl$_4$:CH$_2$Cl$_2$ (95:5). The resulting red solid (~1.1 g) was filtered and was a single spot on TLC. It has $\lambda_{max}^{absorption}$ 512 nm in 0.05 M PO$_4{}^{3-}$ buffer pH 8.0 with $\epsilon$78,200. It has no emission.

Ex. 4. Preparation of 3',6'-dihydroxy-4',5'-dimethoxy-2',7'-diiodospiro[isobenzofuran-1(3H),9'-[9H]xanthen]-5 or 6-carboxy-3-one 4',5'Dimethoxy-6-carboxyfluorescein (Ex. 3) (1.05 g) was dissolved in absolute ethyl alcohol (15 ml) and to this was added I$_2$ powder (1 g) and solid sodium bicarbonate (0.5 g). The contents were refluxed (outside bath temperature 80°–85°) for 1 hr under N$_2$. TLC examination (CH$_2$Cl$_2$:methanol:acetic acid 85:14:1) of the refluxing mixture indicated the formation of monoiodinated and small amounts of diiodinated derivatives along with starting material.

More of I$_2$ (500 mg) and NaHCO$_3$ (250 mg) were added and heating continued for 1 hr more. TLC showed formation of more of the mono- and diiodinated products. The addition of more I$_2$ (500 mg) and NaHCO$_3$ (250 mg) followed by 1 hr heating was repeated two more times. TLC of the final mixture indicated the presence of large amounts of diiodinated derivatives along with traces of monoiodinated derivative.

The ethyl alcohol was removed on a Rotovap. To the white residue was added 20 ml of water and the solution acidified with dilute HCl to pH 1. A brown oil separated out. This was extracted with ether (3×50 ml). The dark red ethereal layer was washed with 5% sodium thiosulphate solution (2×20 ml) followed by water (1×20 ml) and brine solution (1×20 ml). The ether was removed on a Rotovap and the residue dissolved in 4% NaOH (20 ml) and filtered. The filtrate was acidified with dilute HCl to give a dark red solid (2.1 g).

This red solid (2.1 g) was adsorbed on 4 g of RP-2 silica gel silanized (E. Merck Cat. No. 9917) using acetone and then poured over a gravity column of RP-2 silica gel (prepared from 30 g of RP-2 silica gel using CH$_2$Cl$_2$) and eluted with CH$_2$Cl$_2$. Elution was followed by TLC. Fractions having the same Rf were combined and the solvent removed. The residue (~1.1 g) was dissolved in 10 ml of CH$_2$Cl$_2$:MeOH (99:1) and n-hexane (7 ml) was added. A thick precipitate separated out. This was filtered and the mother liquor concentrated; to which more hexane was added to give more solid. The solids were combined (0.95 g) to give 2',7'-diiodo-4',5'-dimethoxy-6-carboxyfluorescein as very light-colored long needles which became orange red on standing.

The product has $\lambda_{max}^{absorption}$ 533 nm in 0.05 M PO$_4{}^{3-}$ buffer pH 8.0 with $\epsilon$81,780.

Ex. 5. Preparation of 9-(2',5',6'-trichloro-3',5'-dicarboxyphenyl)-2,7-dimethoxy-4,5-dichloro-6-hydroxy-3-isoxanthenone A. Into 25 ml of 20% fuming sulfuric acid was dissolved 10 g of 4-methylphthalic anhydride and 0.5 g powdered iodine. The mixture was heated at 90°–100° and chlorine gas was bubbled through the solution continuously. After heating for 24 hrs, an additional 0.5 g of iodine was added and the heating continued for an additional 24 hrs. A white solid had precipitated and the solution was cooled, diluted in 100 ml ice-cold water and the white solids filtered. The solid was washed with 20 ml cold water and dried in vacuo. The product was believed to be a mixture of 3,5,6-trichloro-4-methylphthalic diacid and anhydride.

B. Into a reaction flask was introduced 20 g (0.075 mole) of the above product and 400 ml of aqueous 10% potassium carbonate. After refluxing for about 1 hr at 120°, 20 ml of t-butanol was added, followed by adding 33 g (0.2 mole) powdered potassium permanganate in portions to prevent accumulation of the permanganate. An additional 100 ml of the 10% aqueous potassium carbonate was used to wash in the permanganate. The reaction course was followed by tlc and when the substantial absence of the starting material was observed, the t-butanol was removed by distillation and the resulting slurry acidified with 6 M H$_2$SO$_4$ to pH 1. The excess permanganate was destroyed with solid oxalic acid while the pH was maintained at 1 by the addition of sulfuric acid. After concentration in vacuo, with formation of a white precipitate, 6 M HCl was added to a final volume of 300 ml. After stirring for 30 min at room temperature, a fine white precipitate formed. The slurry was extracted with ether 3×400 ml, the ether solution separated and the ether evaporated in vacuo. After azeotropic drying with benzene, 20 g of white powder was isolated, which was recrystallized from ethyl acetate-CCl$_4$ to yield 19.5 g of the product. mp 238°–240°.

C. The above product (10 g) was dissolved in 30 ml acetic anhydride and heated at 140°–145° under nitrogen for 45 min. The acetic anhydride was removed in vacuo at a temperature of about 35°–40°. The white solid weighed 9.5 g. The product is the mixed anhydride with acetic acid and the intramolecular anhydride of the 1,2-dicarboxylic acid groups.

This product (9.5 g) can be mixed with 12 g of 2-chloro-4-methoxyresorcinol and 1 g of anh. zinc chloride and heated at 185°–190° for about 1.5 hrs. The product is then worked-up as described previously.

Ex. 6. Conjugation of the Product of Example 3 With Anti(human IgG)

A solution of 25 mg of the product of Example 3 in 1 ml dry THF was stirred with dicyclohexyl carbodiimide (10 mg) and 10 mg of NHS overnight. After filtering the solution, the solvent was removed and the residue macerated with 10 ml of n-hexane for 20 min. After filtering the resulting solid and washing the solid with 5 ml n-hexane, the resulting ester was used without further purification. To a 1% solution of anti(human IgG) (10 mg protein) in 1 ml of 0.05 M phosphate buffer, pH 8, was slowly added 0.7 mg of the above NHS ester in 25 $\mu$l DMF and the mixture stirred for 1 hr at 0°–5° and then for an additional hour at room temperature. The product was purified by chromatographing through a G25 Sephadex column using 0.05 M phosphate buffer, pH 8. The total resulting volume was 2.2 ml. Based on UV absorption at 519 nm, the dye/protein ratio was estimated to be about 5.

Ex. 7. Conjugation of the Product of Example 4 With Anti(human IgG)

A. A solution of 4',5'-dimethoxy-2',7'-diiodo-6-carboxyfluorescein (Ex. 4) (250 mg), dicyclohexyl carbodiimide (80 mg) and N-hydroxysuccinimide (50 mg) in freshly distilled dry THF (3 ml) was stirred for 6 hours at room temperature. During this time some white solid separated out which was filtered off. The filtrate was concentrated on a Rotovap and the residue dried for 5 min in vacuo to remove the last traces of solvent. The resulting deep red solid was stirred with 12 ml of benzene-hexane mixture (1:1) for 20 min and the resulting deep violet solid filtered. This solid was found by TLC in $CH_2Cl_2$:MeOH:AcOH (85:15:1) to be almost all NHS ester (as indicated by higher Rf as compared to starting material because the NHS ester reacts with methanol to give the corresponding methyl ester). The violet solid was used as is for conjugation to proteins and is considered to be about 90% pure by weight.

B. To a solution of human-IgG (5 mg in 0.5 ml of 0.05 M $PO_4^{3-}$ buffer containing 1% cholic acid pH 8.0) cooled to 0°–5° in an ice-bath was added a solution of the NHS ester prepared above (0.4 mg) in 25 µl dry DMF slowly during 20 min. Continued stirring overnight in the cold room. Next day, the solution was centrifuged for 2 min and the deep red solution purified over a Sephadex G-25 column (1×30 cm) using 0.05 M $PO_4^{3-}$ buffer pH 8.0 containing 1% cholic acid. The faster moving conjugate was easily separated.

Calculation of the hapten number (i.e., dye/protein ratio) was done as follows. The amount of dye from a UV spectra of a particular dilution is determined by dividing OD at 539 by the extinction coefficient 81,780. The amount of protein is determined by knowing the concentration of protein to start with before conjugation and using that concentration number (with appropriate dilution correction for the final conjugate assuming that no protein is lost during conjugation and Sephadex chromatography).

It is found out that there is about 80–90% labelling efficiency of the NHS ester of the subject quencher when labelled according to the above procedure.

Ex. 8. Preparation of 4,5-dimethoxy-6-hydroxy-9-(2'-carboxyethyl)xanthen-3H-3-one Into a reaction flask was introduced $O^2$-methyl pyrogallol (300 mg), succinic anhydride (100 mg) and $ZnCl_2$ (20 mg) and the mixture heated at 180°–85° for 15 min. The product was purified by preparative TLC ($CH_2Cl_2$:MeOH:AcOH::90:10:0.5), and the purified product had $\lambda_{max}^{absorption}$ 506-7 nm in 0.05 M $PO_4^{3-}$ buffer, pH 8.0, with no fluorescence emission.

Following the above procedure, by substituting the succinic anhydride with other anhydrides such as glutaric anhydride, 2,3-dimethylsuccinic anhydride, 1,2-cyclopentanedicarboxylic acid anhydride and adipic anhydride, one would obtain the appropriately substituted 4,5-dimethoxy-6-hydroxy-9-substituted xanthen-3H-3-one.

Ex. 9. Preparation of 3',6'-dihydroxy-4',5'-dichloro-2',7'-dimethoxyspiro[isobenzofuran-1(3H),9'-[9H]xanthen]-4,7-dichloro-5 or 6-carboxy-3-one A. 2-Chloro-4-methoxyresorcinol (0.4 g) and 3,6-dichlorotrimellitic acid anhydride (0.27 g) was heated with $ZnCl_2$ (10 mg) at 185° for 15 min and the product purified by TLC using $CH_2Cl_2$:MeOH:AcOH::90:10:1. The product had $\lambda_{max}^{absorbance}$ 533 nm and $\lambda_{max}^{emission}$ 549-50 nm in 0.05 M $PO_4^{3-}$ buffer, pH 8.0.

B. The 3,6-dichlorotrimellitic anhydride was prepared as follows:

To a solution of 2,5-dichloro-3,6-dimethylaniline (5 g) in dilute HCl (4 N, 30 ml), maintained at 0° in a three necked flask equipped with a mechanical stirrer, was added dropwise a solution of sodium nitrite (1.85 g in 50 ml water). After the addition was complete, the diazo solution was neutralized with $Na_2CO_3$ to pH 7 and benzene (100 ml) added. To this was then added a freshly prepared solution of cuprous cyanide [prepared from a solution of cuprous chloride and sodium cyanide[ with vigorous stirring. The mixture was allowed to come to room temperature and then stirred overnight. Next day, the benzene layer was separated and concentrated to give about 4.5 g of crude brown solid as the nitrile. This was not purified but hydrolyzed directly to the amide. A solution of the nitrile (4.5 g) in a mixture of dioxane (30 ml) and 4% aq. NaOH (70 ml) was refluxed for 8 hrs. The solution was cooled, extracted with ether and the ethereal solution concentrated to give a brown oil which on maceration with chloroform yielded a brown solid. This was crystallized from chloroform-petroleum ether to give the amide (2.3 g).

To a solution of the above amide (0.9 g) in conc. $H_2SO_4$ (4 ml) was added slowly a solution of sodium nitrite (0.37 g in 1 ml of water); while maintaining the temperature of the solution below 30°. After the addition was complete, the mixture was diluted with ice to give a white precipitate which was filtered and further purified by dissolving in 10% $K_2CO_3$ solution, filtering and acidification with 1 N HCl to give 2,5-dichloro-3,6-dimethylbenzoic acid.

To the above prepared acid (0.56 g) was added alkaline $KMnO_4$ (1.81 g in 10 ml of 10% $K_2CO_3$) and the mixture heated at 110° for 3 hrs. The resulting mixture was acidified with 6 N $H_2SO_4$ to pH 1 and excess $KMnO_4$ removed by treatment with oxalic acid. Extraction with ether gave the required triacid product, m.p. 232°–33°.

Ex. 10. Preparation of 2,7-di(methylthio)-6-hydroxy-9-(2'-carboxyphenyl)xanthen-3H-3-one Into a reaction flask was introduced 4-thiomethylresorcinol (200 mg), phthalic anhydride (104 mg) and zinc chloride (10 mg) and the mixture heated at 180° for 5 min. The product was purified by preparative TLC using $CH_3OH$:$CH_2Cl_2$:HOAc (9:1:0.1) and the resulting product had $\lambda_{max}^{absorption}$ 512 nm and $\lambda_{max}^{emission}$ 540 nm in 0.05 M $PO_4^{3-}$ buffer, pH 8.0.

In order to demonstrate the utility of the subject compounds, the protein conjugates were employed in an immunoassay as described in U.S. Pat. No. 3,996,345. In the first assay, a conjugate of fluorescein isothiocyanate and human IgG having a fluorescein/protein mole ratio of about 7 was employed at a concentration of 0.03 mg/ml. The product of Example 6 was employed at a concentration of 4.9 mg/ml in 0.05 M phosphate buffer, pH 8. Varying dilutions of the product of Example 6 were added to a fixed amount of the fluorescein conjugate and incubated for 10 min employing as the assay buffer, 0.01 M phosphate, 0.15 M NaCl and 2% PEG, pH 8.0. The protocol followed was to combine 25 µl of the fluorescein conjugate in 250 µl of buffer with 25 µl of the appropriately diluted product of Example 6 in 250 µl of buffer, incubate the mixture for 10 min, add 2 ml of the buffer and then determine the fluorescent signal. When the fluorescein-IgG conjugate was replaced with buffer, so as to obtain background derived from the product of Example 6, the fluorescent signal varied from 0 to 6 with the various dilutions of the product of Example 6, indicating that there was no fluorescence, the observed fluorescence being well within instrumental error.

The following table indicates the results, indicating the various dilutions and the observed fluorescence.

TABLE II

| Dilution of Ex. 6 | Fluorescent Signal |
|---|---|
| 1:40 | 722 |
| 1:20 | 598 |
| 1:10 | 382 |
| 1:5 | 198 |
| 1:2.5 | 122 |
| ∞ | 928 |

The above results demonstrate, that the conjugates of the subject invention provide for a large dynamic range in change in fluorescence depending upon the concentration of the quencher conjugate in relation to the fluorescein present in the medium. The subject data demonstrate that a sensitive assay for gamma-globulin is available, since by adding gamma-globulin to the medium, the amount of available quencher-conjugate for binding to the fluorescer conjugate would be diminished in proportion to the amount of antigen present in the assay medium. Furthermore, by employing the conjugate of the subject invention, background radiation from the subject quencher conjugate is essentially absent.

A second assay was performed, replacing the quencher conjugate of Example 6 with the quencher conjugate of Example 7. The mole ratio of quencher to protein was about 1.5 and the concentration of the quencher solution was approximately 4 mg/ml. Instead of fluorescein, the fluorescer employed was 2,7-dimethyl-9(2′,5′,6′-trichloro-3′,4′-dicarboxyphenyl)-6-hydroxy-3-isoxanthenone. This compound was linked through one of the carboxyl groups to IgG through a glycine linking group. The fluorescer/protein mole ratio was about 7.5, and the solution had a concentration of about 0.03 mg/ml. The assay described previously was performed with both the quencher of the subject invention, Example 7, and commercially available rhodamineisothiocyanate conjugated to antiIgG. The following table indicates a comparison of the results observed with the two quenchers.

TABLE III

| | Ex.7 | Rhodamine Conjugate |
|---|---|---|
| λ excitation, nm | 520 | 520 |
| λ emission (abs), nm | 550 | 550 |
| Quencher/Protein (mole ratio) | ~1.5 | ~7 |
| Max. Quenching w/1:5 antibody dilution, % | 65–70 | 94 |
| Bkgd. Signal due to Quencher, % of Fluorescer Signal | 6–10 | 60–90 |

(The fluorescer compound described above was prepared from 4-methylresorcinol and 2,5,6-trichloro-1,3,4-phenyltricarboxylic acid anhydride in the manner described previously for the preparation of fluorescein derivatives).

The next assay performed was for the hapten, morphine. 6-Carboxyfluorescein NHS ester was conjugated with $O^3$-(2′-aminoethyl) morphine and the compound of Ex. 3 conjugated to antimorphine at varying dye/antibody ratios as described in Ex. 6.

The fluorescent signal from the morphine conjugate was plotted against the concentration of antimorphine conjugate. The assay mixture contained 8.75 ng/2.55 ml of the fluorescer-morphine conjugate. The antimorphine conjugate was added in amounts varying from 0 to 125 μg, with varying ratios of quencher to antimorphine. The buffer employed for the assay mixture 0.01 M $PO_4^{3-}$ 0.15 M NaCl and 2% PEG 6000. The fluorescein was measured with a Perkin-Elmer 1000 at a concentration of antimorphine-quencher conjugate (based on protein) of 50 μg/2.55 ml.

| D/P ratio[1] | Fluoroescent Signal[2] |
|---|---|
| 1 | 715 |
| 3.4 | 400 |
| 7.8 | 110 |
| 10 | 80 |

[1]D/P-quencher/protein mole ratio.
[2]Signal based on 1000 for no antimorphine-quencher conjugate.

By adding morphine to the assay mixture, the fluorescence was enhanced, demonstrating the specificity of the quenching effect.

In comparison to the commonly employed rhodamine as a quencher, the subject quenchers do not have many of the deficiencies of rhodamine and comparable dyes employed as quenchers. Rhodamine has two absorption maxima when conjugated with proteins, with the ratio of the two maxima varying with the degree of labelling. For effective quenching high rhodamine/antibody ratios are required which causes insolubility. This requires the addition of undesirable solubilizing agents e.g. cholic acid or glycerol.

It is evident from the above results that with much lighter labeling than rhodamine, highly efficient quenching is achieved with the conjugate according to the subject invention. Furthermore, the contribution to background is much smaller than that observed with rhodamine. Thus, one can develop an efficient assay with a high degree of quenching and a minimum amount of interference from light radiated by the quencher.

The quencher conjugate has additional advantages in that it is efficiently conjugated and is quite soluble in the assay medium as compared to rhodamine, which has been previously taught and is conventionally used as a quencher for fluorescein. Furthermore, because of the excellent overlap between the emission of the fluorescer and the absorption of the quencher, high efficiency transfer is achieved. Also, the compounds are easily synthesized and readily conjugated to proteins and other ligands. Finally, precipitation is not observed at the levels of labeling employed, so that this problem which was observed with rhodamine is precluded.

It is evident from the above results, that the compositions of the subject invention, both the parent fluorescein derivative quenchers and their conjugates with protein are highly advantageous for use in assays. The compounds are water soluble and can be readily conjugated to proteins. When conjugated to proteins, for example, antibodies, they provide useful reagents in immunoassays where quenching of a fluorescer is necessary. The quenchers of the subject invention provide for highly efficient quenching of the fluorescer, while making only a small or negligible contribution to the amount of light observed from the assay medium.

The fluorescent compounds of this invention absorb at longer wave lengths, so that they can be excited with light which has little, if any, exciting effect on naturally occurring fluorescers encountered in assay samples, e.g. serum. The compounds are water soluble and when conjugated to proteins do not undergo significant changes in the spectroscopic properties of interest. In addition, the compounds have large Stokes shifts, sharp absorption and emission peaks, and good chemical and thermal stability.

Although the foregoing invention has been described in some detail by way of illustration and example for purposes of clarity of understanding, it will be obvious that certain changes and modifications may be practiced within the scope of the appended claims.

What is claimed is:

1. A chromogenic compound capable of donating or accepting electronic energy, which is a 2,7-di(aliphatic chalcogen ether substituted) or 4,5-di(aliphatic chalcogen ether substituted)-9-substituted-6-hydroxy-3H-xanthen-3-one, wherein chalcogen is of atomic number 8 to 16, conjugated to a poly(amino acid).

2. A chromogenic compound according to claim 1, which is a 2,7-di(alkoxy substituted)-9-phenyl-6-hydroxy-3H-xanthen-3-one, conjugated to a poly(amino acid).

3. A chromogenic compound according to claim 1, which is a 4,5-di(alkoxy substituted)-9-phenyl-6-hydroxy-3H-xanthen-3-one, conjugated to a poly(amino acid).

4. A compound of the formula:

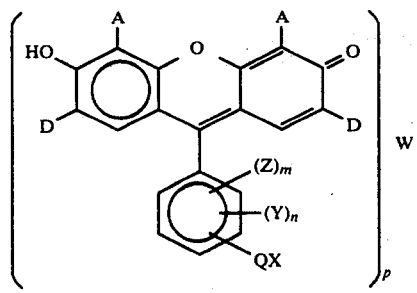

wherein:
the As are the same or different;
the Ds are the same or different;
either the As or the Ds are ethers of the formula —JMX, wherein J is chalcogen of atomic number 8 to 16; when other than JMX they are hydrogen, or halogen of atomic number 9 to 53;
M is a divalent hydrocarbon group of from 1 to 8 carbon atoms;
W is a poly(amino acid);
one of the Xs is a linking functionality to W; the other X being hydrogen or non-oxo-carbonyl with the proviso that when X is bonded to an annular carbon atom, X can be halo;
Q is a bond or spacer arm;
Y is halogen of atomic number 9 to 53;
Z is an acidic anionic group;
m is an integer of from 0 to 3;
n is an integer of from 0 to 4, wherein m plus n is not greater than 4;
p is 1 to the molecular weight of W divided by 500.

5. A compound according to claim 4, wherein —JMX is alkoxy of from 1 to 3 carbon atoms.

6. A compound according to claim 5, wherein the As are alkoxy.

7. A compound according to claim 5, wherein the Ds are alkoxy.

8. A compound of the formula:

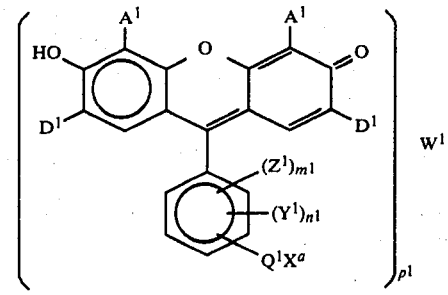

wherein:
the $A^1$s are the same and the $D^1$s are the same; and either the $A^1$s or the $D^1$s are oxyethers of the formula —$OR^bX^b$; when other than —$PR^bX^b$, they are hydrogen or halogen of atomic number 9 to 53;
wherein $R^b$ is saturated aliphatic hydrocarbon of from 1 to 3 carbon atoms;
one of $X^a$ and $X^b$ is a linking functionality to $W^1$, wherein said linking functionality including a non-oxo-carbonyl or the sulfur analog thereof;
when other than a linking functionality, $X^b$ is hydrogen or carboxyl and $X^a$ is hydrogen, carboxyl or halo of atomic number 9 to 53;
$Q^1$ is a bond or a spacer arm, being a bond when $X^a$ is other than a linking functionality; when $Q^1$ is a spacer arm, it has a chain of from 1 to 16 atoms which are carbon, oxygen and nitrogen, wherein heteroatoms are spaced apart by at least two carbon atoms when bonded to saturated carbon atoms;
$Z^1$ is a carboxylic acid or sulfonic acid group;
$Y^1$ is halogen of atomic number 9 to 53;
$m^1$ is an integer from 1 to 2;
$n^1$ is an integer from 0 to 4, wherein $m^1$ plus $n^1$ is not greater than 4;
$W^1$ is a poly (amino acid).

9. A compound according to claim 8, wherein the $A^1$s are alkoxy of from 1 to 3 carbon atoms.

10. A compound according to claim 8, wherein the $D^1$s are alkoxy of from 1 to 3 carbon atoms.

11. A compound according to any of claims 9 or 10, wherein $X^a$ is a carbonyl.

12. A compound according to the formula:

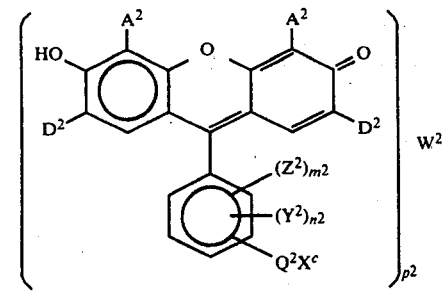

wherein:

either the $A^2$s or the $D^2$s are alkoxy of from 1 to 3 carbon atoms; when other than alkoxy, they are hydrogen or halogen of atomic number 9 to 53;

$Y^2$ is halogen of atomic number 9 to 53;

$Z^2$ is carboxyl;

$m^2$ is an integer of from 1 to 2;

$n^2$ is an integer of from 0 to 4, wherein $m^2$ plus $n^2$ is not greater than 4;

$Q^2$ is a bond or spacer arm of from 1 to 12 atoms in the chain, which are carbon, nitrogen and oxygen;

$X^c$ is a non-oxo-carbonyl containing linking group including the sulfur analog thereof;

$W^2$ is a poly(amino acid);

$p^2$ is at least 1 and up to the molecular weight of $W^2$ divided by 500.

13. A compound according to claim 12, wherein said poly(amino acid) is a hapten of from about 125 to 1000 molecular weight.

14. A compound according to claim 12, wherein said poly(amino acid) is an antigen of at least about 5000 molecular weight.

15. A compound according to any of claims 13 and 14, wherein $A^2$ is alkoxy of from 1 to 3 carbon atoms, $D^2$ is hydrogen or halogen of atomic 9 to 53, $Q^2$ is a bond or spacer arm of from 1 to 12 atoms in the chain, $X^c$ is carbonyl bonded to an amino group of $W^2$ to form an amide; and $p^2$ is about 1 to 100.

16. A compound of the formula:

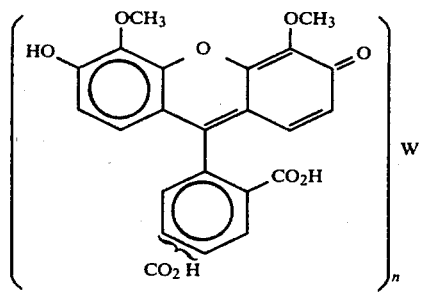

wherein W is a poly(amino acid), and n is one to the molecular weight of W divided by 500.

17. A compound of the formula:

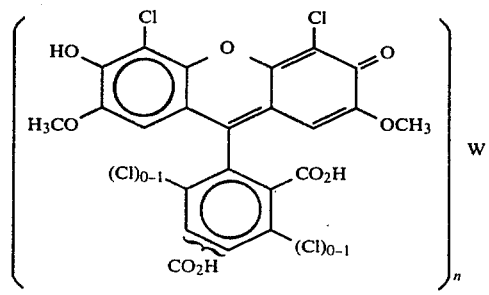

wherein W is a poly(amino acid) and n is 1 to the molecular weight of W divided by 500.

18. A compound of the formula:

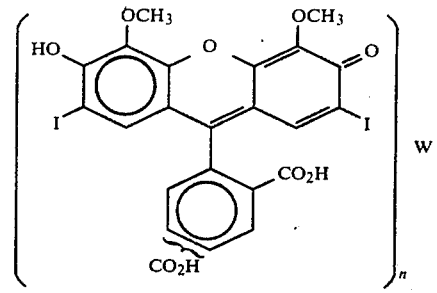

wherein W is a poly(amino acid) and n is 1 to the molecular weight of W divided by 500.

19. A compound of the formula:

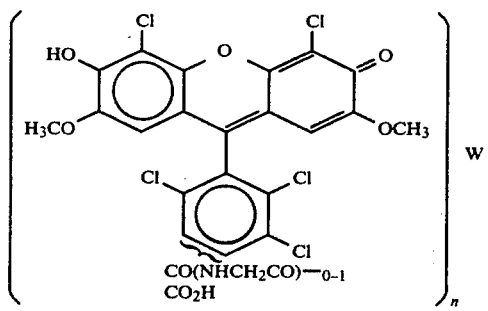

wherein W is a poly(amino acid) and n is 1 to the molecular weight of W divided by 500.

20. A compound of the formula:

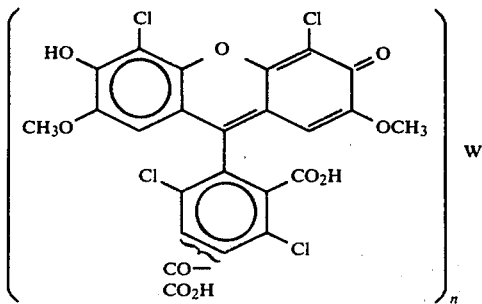

wherein W is a poly(amino acid) and n is 1 to the molecular weight of W divided by 500.

21. A compound according to any of claims 16, 17, 18, 19, or 20, wherein said poly(amino acid) is an antigen.

22. A compound according to any of claims 16, 17, 18, 19, or 20, wherein said poly(amino acid) is an antibody.

* * * * *